United States Patent [19]

Dickoré et al.

[11] Patent Number: 4,846,881
[45] Date of Patent: Jul. 11, 1989

[54] 3,4,6-TRISUBSTITUTED 1,2,4-TRIAZIN-5(4H)-ONE HERBICIDES

[75] Inventors: Karlfried Dickoré; Hans-Joachim Santel, both of Leverkusen; Robert R. Schmidt, Gladbach; Harry Strang, Duesseldorf, all of Fed. Rep. of Germany

[73] Assignee: Bayer Aktiengesellschaft, Leverkusen, Fed. Rep. of Germany

[21] Appl. No.: 168,714

[22] Filed: Mar. 16, 1988

[30] Foreign Application Priority Data

Mar. 28, 1987 [DE] Fed. Rep. of Germany ....... 3710255

[51] Int. Cl.$^4$ .................. A01N 43/707; C07D 253/06
[52] U.S. Cl. .......................................... 71/93; 544/182
[58] Field of Search ............................. 544/182; 71/93

[56] References Cited

U.S. PATENT DOCUMENTS 3,671,523  6/1972  Westphal et al. ................... 544/182

FOREIGN PATENT DOCUMENTS 0130518  1/1985  European Pat. Off. .
0150677  8/1985  European Pat. Off. .
1542873  7/1970  Fed. Rep. of Germany .
2417511  10/1975  Fed. Rep. of Germany .
2856750  7/1980  Fed. Rep. of Germany .
3240308  5/1984  Fed. Rep. of Germany .

Primary Examiner—John M. Ford
Attorney, Agent, or Firm—Sprung, Horn, Kramer & Woods

[57] ABSTRACT

Herbicidal 3,4,6-trisubstituted 1,2,4-triazin-5(4H)-ones of the formula

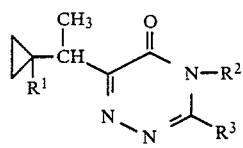

in which
$R^1$ represents hydrogen or methyl,
$R^2$ represents amino, methylamino or methyl and
$R^3$ represents methylthio, ethylthio, methylamino, ethylamino, allylamino, dimethylamino, methylethylamino or diethylamino.

Novel intermediates therefor are also shown.

12 Claims, No Drawings

3,4,6-TRISUBSTITUTED 1,2,4-TRIAZIN-5(4H)-ONE HERBICIDES

The invention relates to new 3,4,6-trisubstituted 1,2,4-triazin-5(4H)-one derivatives, processes for their preparation and their use as herbicides.

It has already been disclosed that certain substituted 1,2,4-triazin-5(4H)-one derivatives such as, for example, 4-amino-6-tert.-butyl-3-methylthio-1,2,4-triazin-5(4H)-one can be used as herbicides (cf. German Pat. No. 1,542,873; U.S. Pat. No. 3,671,523). In certain crops, however, selective employment of the previously known triazinones is not possible since damage may also result in certain useful plants on account of the uniformly high herbicidal potency of this group of substances; tolerance towards the previously known triazinones is therefore not sufficient in various useful plants.

The new 3,4,6-trisubstituted 1,2,4-triazin-5(4H)-ones of the formula (I)

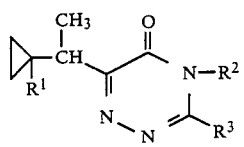

(I)

in which
R¹ represents hydrogen or methyl,
R² represents amino, methylamino or methyl and
R³ represents methylthio, ethylthio, methylamino, ethylamino, allylamino, dimethylamino, methylethylamino or diethylamino,
have now been found.

Furthermore it has been found that the new 3-alkylthiotriazinone derivatives of the formula (Ia)

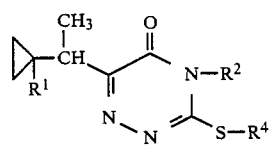

(Ia)

in which
R¹ and R² have the meanings given above and
R⁴ represents methyl or ethyl,
are obtained when 5-oxo-3-thioxo-tetrahydro-1,2,4(2H,4H)-triazines of the formula (II)

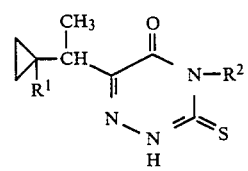

(II)

in which
R¹ and R² have the meanings given above, are alkylated in a manner known per se in alkaline solution by means of a methyl or ethyl halide (preferably iodide or bromide) (process A).

It has furthermore been found that the new 3-aminotriazinone derivatives of the formula (Ib)

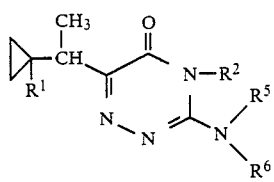

(Ib)

in which
R¹ and R² have the meanings given above,
R⁵ represents hydrogen, methyl or ethyl and
R⁶ represents methyl, ethyl or allyl,
are obtained when
(a) 3-alkylthio-triazinone derivatives of the formula (Ia) are reacted with an amine of the formula (III)

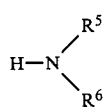

(III)

in which
R⁵ and R⁶ have the meanings given above, optionally in the presence of a diluent and optionally in the presence of a lower aliphatic carboxylic acid (process B), or when
(b) an α-keto or α-thioketo carboxylic acid of the formula (IV)

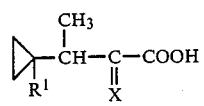

(IV)

in which
R¹ has the meaning given above and
X represents oxygen or sulphur,
is reacted in aqueous solution with an aminoguanidine salt of the formula (V)

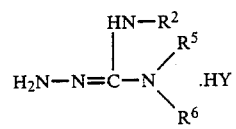

(V)

in which
R², R⁵ and R⁶ have the meanings given above and
Y represents Cl, Br or I (process C).

In addition it has been found that the new 3-alkylthio-4-methylamino-triazinone derivatives of the formula (Ic)

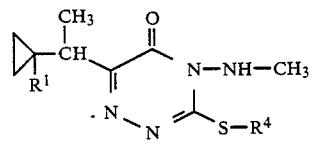

(Ic)

in which
R¹ and R⁴ have the meanings given above, can also be prepared by reacting a 3-alkylthio-4-aminotriazonone derivative of the formula (Id)

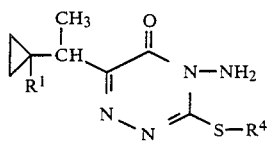
(Id)

in which

R[1] and R[4] have the meanings given above, in a manner known per se with a methylating agent of the formula (VI)

(VI)

in which

Z represents Br, I or $CH_3SO_4$, in the presence of a phase-transfer catalyst (process D).

Moreover it has been found that the new 3,4,6-trisubstituted 1,2,4-triazin-5(4H)-ones of the formula (I) exhibit good herbicidal properties, in particular selective herbicidal properties.

Surprisingly, the compounds according to the invention exhibit, in particular, better compatibility with important crop plants, such as barley, corn and others, besides improved general herbicidal activity in contrast with the known 4-amino-6-tert.-butyl-3-methylthio-1,2,4-triazin-5(4H)-one, which is a related compound structurally and in respect of activity. The active compounds according to the invention therefore represent an enrichment of the range of herbicidal agents, particularly to the selective chemical combating of weeds.

The triazinone derivatives according to the invention are generally defined by the formula (I). Those compounds of the formula (I) wherein R[1] represents hydrogen, R[2] represents amino or methylamino and R[3] represents methylthio, methylamino or dimethylamino are particularly preferred triazinone derivatives.

If, for example, 4-amino-6-(1-cyclopropylethyl)-5-oxo-3-thioxo-tetrahydro-1,2,4(2H,4H)-triazine is used as a starting material and methyl iodide as an alkylating agent, then the course of the reaction according to process A can be represented by the following equation:

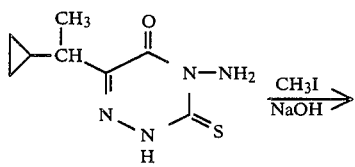

If the 4-amino-6-(1-cyclopropylethyl)-3-methylthio-1,2,4-triazin-5(4H)-one thus obtained and monomethylamine are used as starting materials, then the course of the reaction according to process B can be represented by the following equation:

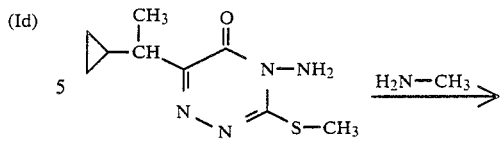

If, for example, 1-cyclopropylethyl-thionoglyoxylic acid and 1-amino-2,2,3-trimethylguanidine hydrochloride are used as starting materials, then the course of the reaction according to process C can be represented by the following equation:

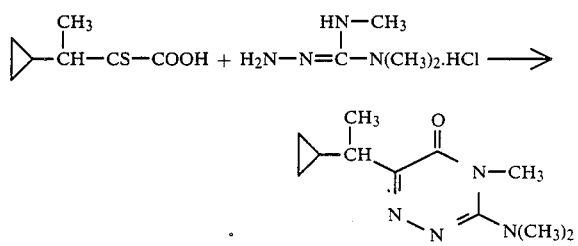

If, for example, 4-amino-6-(1-cyclopropylethyl)-3-methylthio-1,2,4-triazin-5-(4H)-one and methyl iodide are used as starting materials, then the course of the reaction according to process D can be represented by the following equation:

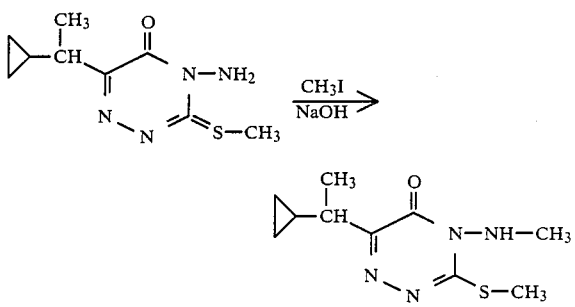

phase-transfer catalyst

The compounds of the formula (II) used as starting materials are not yet known.

They can be prepared in a manner known per se by reacting an α-keto or α-thioketo carboxylic acid of the formula (IV) with a thiocarbohydrazide or thiosemicarbazide of the formula (VII):

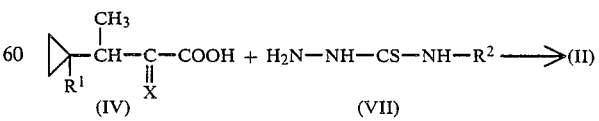

R[1], R[2] and X here have the meanings given above.

The α-keto or α-thioketo carboxylic acids of the formula (IV) are also not yet known.

The α-keto carboxylic acids (IV, X=O) can be prepared, for example, by condensation of the known methylcyclopropyl ketones with hippuric acid and saponification of the "azlactones" obtained (ERLENMEYER reaction):

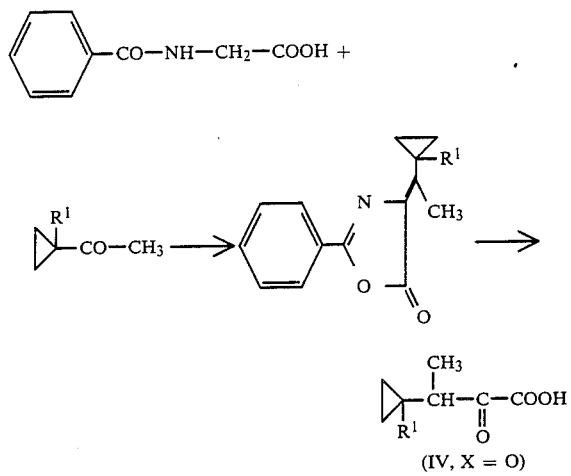

A process of good technical practicability for the preparation of the α-thioketo carboxylic acids (IV, X=S) is based on the condensation of methyl cyclopropyl ketones with N-methylrhodanine and subsequent alkaline hydrolysis of the alkylidene-N-methylrhodanines thus obtained (variation of the GRÄNACHER reaction). The condensation of the unisolated α-thioketo carboxylic acids of the formula (IV, X=S) with thiosemicarbazides or thiocarbohydrazides yields 6-(1-cyclopropylethyl)-5-oxo-3-thioxo-tetrahydro-1,2,4(2H,4H)-triazines of the formula (II):

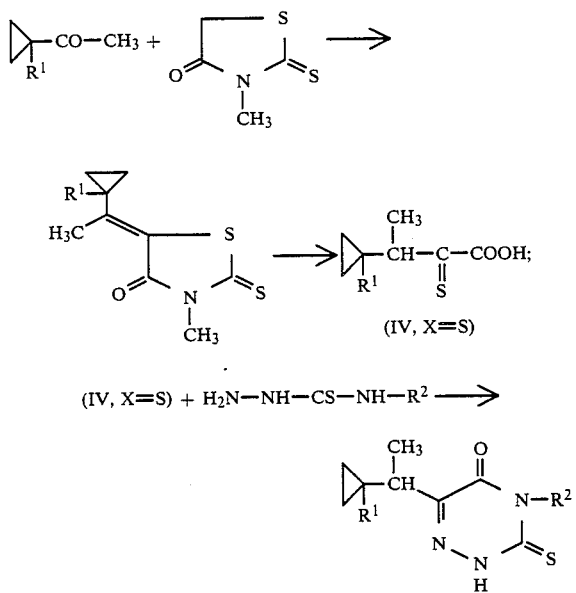

The thiosemicarbazides used here are known; thiocarbohydrazide is also known.

1-methyl-thiocarbohydrazide on the contrary is not yet known. It can be prepared by reaction of 1-tert.-butoxycarbonyl-1-methylhdrazine (cf. Acta chem., scand. 22, pp. 1–50 (1968)), with methyl isopropylidene dithiocarbazinate and hydrolysis of the resulting 1-tert.-butoxycarbonyl-1-methyl-5-isopropylidene thiocarbohydrazide (cf. preparation examples):

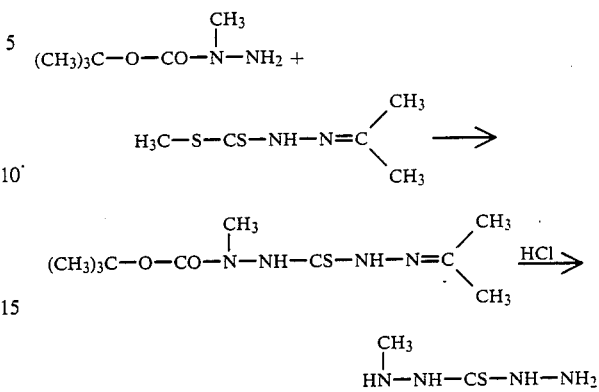

The alkylation of 6-(1-cyclopropylethyl)-5-oxo-3-thioxotetrahydro-1,2,4(2H,4H)-triazines of the formula (II) according to process A is carried out in the presence of a base. Alkali hydroxides, such as sodium hydroxide or potassium hydroxide in aqueous solution are preferably employed here. It has proved appropriate to add small amounts of an alkylaryl polyglycol ether as an emulsifier. Alkali metal alcoholates, such as sodium methylate, can also be used as bases and alcohols can be used as solvents.

The reaction temperatures can be varied over a relatively large range in carrying out process A. In general temperatures between 0° C. and 100° C., preferably between 0° C. and 50° C. are used.

In carrying out the alkylation according to process A, 1 to 1.5 mols of alkylating agent is preferably employed per mol of the intermediate product of the formula (II). The isolation of the intermediate products or end products of the formula (Ia) takes place in the usual manner.

In the reaction of the 3-alkylthio-triazinones of the formula (Ia) with amines of the formula (III) according to process B all inert organic solvents are suitable as diluents. These include hydrocarbons such as toluene and xylene; chlorinated aromatic hydrocarbons such as chlorobenzene, 1,2-dichlorobenzene and 1,2,4-trichlorobenzene; ethers such as tetrahydrofuran and dioxane; alcohols such as methanol, ethanol, propanol and isopropanol; amides such as N,N-dimethylformamide, tetramethyl urea or sulphoxides such as dimethylsulphoxide. Isopropanol is preferably used for the reaction.

The reaction temperatures in process B can be varied over a relatively large range. In general temperatures between about 20° C. and about 170° C., preferably between 60° C. and 90° C., are used.

The reaction can be performed under normal pressure as well as under increased pressures.

A particularly advantageous embodiment of process B consists in working in the presence of at least the equimolar amount of a lower aliphatic carboxylic acid. Acetic acid is preferably used for this. This process allows the use of a relatively low excess of dimethylamine. In this embodiment the reaction rate can be increased by the addition of a catalytic amount of an organic sulphonic acid. P-toluenesulphonic acid is preferably used here.

In carrying out process B according to the invention, in accordance with this preferred process variation, 1 to 2 mols of a lower aliphatic carboxylic acid, 0.01 to 2 mols of an organic sulphonic acid and 1 to 2 mols of dimethylamine are advantageously employed per mol of a 3-alkylthio-triazinone of the formula (Ia), and the mixture is heated until mercaptan cleavage ceases and then worked up. This can be done, for example, by evaporating the mixture, stirring the residue with excess aqueous mineral acid and separating off undissolved impurities. The reaction product is precipitated in high purity by addition of an excess amount of a base, for example ammonia.

Process C is carried out in aqueous solution. An alkaline solution of an α-keto or α-thioketo carboxylic acid of the formula (IV) is advantageously employed, such as results, for example, from the saponification of an azlactone or of an alkylidene-N-methylrhodanine.

The reaction temperatures in the case of process C can likewise be varied over a relatively large range. In general temperatures between about 50° C. and about 100° C., preferably between 65° C. and 90° C., are used.

Process C is in general carried out under normal pressure.

In carrying out process C, 1 to 1.1 mols of an aminoguanidinium salt of the formula (V) is employed per mol of an aqueous solution of the Na salt of the α-keto or α-thioketo carboxylic acid (IV) concerned, and the mixture is heated after the addition of mineral acid, for example hydrochloric acid, until the end of the reaction. Working up is then performed in the same manner as for process B.

Process D is carried out in a two-phase system. Besides water, a water-immiscible solvent such as, for example, benzene, toluene, xylene or chlorobenzene is used. Toluene is preferably used. In carrying out process D 1–5 mols of a methylating agent such as methyl bromide, methyl iodide or dimethylsulphate is employed per mol of 4-amino-6-(1-cyclopropylethyl)-3-methylthio-1,2,4-triazin-5(4H)-one. Preferably 2–4 mols of methyl iodide are used. Moreover, 0.01 to 0.2 mol of a quaternary ammonium salt, preferably 0.08 to 0.12 mol of tetrabutylammonium bromide, is added as a phase-transfer catalyst.

The reaction temperatures can also be varied over a relatively large range in process D. In general temperatures between 0° C. and 100° C., preferably 20° C. to 100° C., are used.

The active compounds according to the invention influence plant growth and can therefore be used as defoliants, desiccants, agents for destroying broad-leaved plants and, especially, weed-killers. By weeds, in the broadest sense, there are to be understood all plants which grow in locations where they are undesired. Whether the substances according to the invention act as total or selective herbicides depends essentially on the amount applied.

The active compounds according to the invention can be used, for example, in connection with the following plants:

Dicotyledon weeds of the genera: Sinapis, Lepidium, Galium, Stellaria, Matricaria, Anthemis, Galinsoga, Chenopodium, Urtica, Senecio, Amaranthus, Portulaca, Xanthium, Convolvulus, Ipomoea, Polygonum, Sesbania, Ambrosia, Cirsium, Carduus, Sonchus, Solanum, Rorippa, Rotala, Lindernia, Lamium, Veronica, Abutilon, Emex, Datura, Viola, Galeopsis, Papaver and Centaurea.

Dicotyledon crops of the genera: Gossypium, Glycine, Beta, Daucus, Phaseolus, Pisum, Solanum, Linum, Ipomoea, Vicia, Nicotiana, Lycopersicon, Arachis, Brassica, Lactuca, Cucumis and Cucurbita.

Monocotyledon weeds of the genera: Echinochloa, Setaria, Panicum, Digitaria, Phleum, Poa, Festuca, Eleusine, Brachiaria, Lolium, Bromus, Avena, Cyperus, Sorghum, Agropyron, Cynodon, Monochoria, Fimbristylis, Sagittaria, Eleocharis, Scirpus, Paspalum, Ischaemum, Sphenoclea, Dactyloctenium, Agrostis, Alopecurus and Apera.

Monocotyledon crops of the genera: Oryza, Zea, Triticum, Hordeum, Avena, Secale, Sorghum, Panicum, Saccharum, Ananas, Asparagus and Allium.

However, the use of the active compounds according to the invention is in no way restricted to these genera, but also extends in the same manner to other plants.

The compounds are suitable, depending on the concentration, for the total combating of weeds, for example on industrial terrain and rail tracks, and on paths and squares with or without tree plantings. Equally, the compounds can be employed for combating weeds in perennial cultures, for example afforestations, decorative tree plantings, orchards, vineyards, citrus groves, nut orchards, banana plantations, coffee plantations, tea plantations, rubber plantations, oil palm plantations, cocoa plantations, soft fruit plantings and hopfields, and for the selective combating of weeds in annual crops.

It has been shown that the active compounds according to the invention, applied by the post-emergence method, are well tolerated by corn and better tolerated by barley than 4-amino-6-tert.-butyl-3-methylthio-1,2,4-triazin-5(4H)-one (Metribuzin). Moreover the new active compounds are considerably more active than Metribuzin against dicotyledon weeds at lower doses; they can therefore be employed with better results than Metribuzin for weed control in corn and cereals, especially in barley. Other crops in which the new active compounds can be selectively employed are: soy beans, potatoes, peas and lucerne.

The active compounds can be converted to the customary formulations, such as solutions, emulsions, wettable powders, suspensions, powders, dusting agents, pastes, soluble powders, granules, suspension/emulsion concentrates, natural and synthetic materials impregnated with active compound and also very fine capsules in polymeric substances.

These formulations are produced in known manner, for example by mixing the active compounds with extenders, that is liquid solvents and/or solid carriers, optionally with the use of surface-active agents, that is emulsifying agents and/or dispersing agents and/or foam-forming agents. In the case of the use of water as an extender, organic solvents, for example, can also be used as auxiliary solvents. As liquid solvents, there are suitable in the main: aromatics, such as xylene, toluene or alkylnaphthalenes, chlorinated aromatics and chlorinated aliphatic hydrocarbons, such as chlorobenzenes, chloroethylenes or methylene chloride, aliphatic hydrocarbons, such as cyclohexane or paraffins, for example mineral oil fractions, mineral and vegetable oils, alcohols, such as butanol or glycol and their ethers and esters, ketones, such as acetone, methyl ethyl ketone, methyl isobutyl ketone or cyclohexanone, strongly polar solvents, such as dimethylformamide and dimethylsulphoxide, and water.

As solid carriers there are suitable: for example ground natural minerals, such as kaolins, clays, talc, chalk, quartz, attapulgite, montmorillonite or diatomaceous earth, and ground synthetic minerals, such as highly disperse silicic acid, alumina and silicates; as solid carriers for granules there are suitable: for example crushed and fractionated natural minerals such as calcite, marble, pumice, sepiolite and dolomite, synthetic granules of inorganic and organic meals, and granules of organic material such as sawdust, coconut shells, corn cobs and tobacco stalks; as emulsifying and/or foam-forming agents there are suitable: for example non-ionic and anionic emulsifiers, such as polyoxyethylene-fatty acid esters, polyoxyethylene-fatty alcohol ethers, for example alkylaryl polyglycol ethers, alkylsulphonates, alkyl sulphates, aryl sulphonates and albumin hydrolysis products; as dispersing agents there are suitable: for example ligninsulphite waste liquors and methyl cellulose.

Adhesives such as carboxymethylcellulose and natural and synthetic polymers in the form of powders, granules or latices, such as gum arabic, polyvinyl alcohol and polyvinyl acetate, may be used in the formulations.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 percent by weight of active compound, preferably between 0.5 and 90%.

The active compounds according to the invention can be used for combating weeds as such or, in the form of their formulations, also as mixtures with known herbicides, finished formulations or tank mixes being possible.

Known herbicides can be used for these mixtures, for example triazines such as atrazine, ureas such as methabenzthiazuron, chlortoluron or isoproturon, and additionally bromoxynil and ioxynil, or growth promoters such as 2,4-D, MCPP and related compounds, or graminicides, such as diclofop-methyl and the R-enantiomer of (trimethylsilyl)-methyl 2-{4-[(3,5-dichloro-2-pyridinyl)-oxy]phenoxy}propionate.

Mixtures with other known active compounds, such as fungicides, insecticides, acaricides, nematicides, bird repellents, growth promoters, plant nutrients and agents which improve soil structure, are also possible.

The active compounds can be used as such, in the form of their formulations or in the use forms prepared therefrom by further dilution, such as ready-to-use solutions, suspensions, emulsions, powders, pastes and granules. They are used in a customary manner, for example by watering, spraying, sprinkling, atomizing or scattering.

The active compounds according to the invention can be applied either before or after emergence of the plants. The application is preferably performed after the emergence of the plants, i.e. in the post-emergence method. They can also be incorporated into the soil before sowing.

The amount of active compound used can vary within a substantial range. It depends essentially on the nature of the desired effect. In general, the amounts used are between 0.01 and 10 kg of active compound per ha, preferably between 0.03 and 2 kg/ha.

Some of the active compounds according to the invention are also active as defoliants for cotton.

The examples which follow serve to illustrate the invention further.

PREPARATION EXAMPLES

Example 1

4-Amino-6-(1-cyclopropylethyl)-3-methylthio-1,2,4-triazin-5(4H)-one (according to process A):

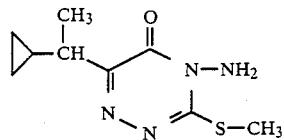

789 g (3.72 mols) of 4-amino-6-(1-cyclopropylethyl)-5-oxo-3-thioxo-tetrahydro-1,2,4-(2H,4H)-triazine are dissolved in a solution of 151 g (3.77 mols) of sodium hydroxide in 4 l of water. 3 ml of alkylarylpolyglycol ether are added, the mixture is cooled to 10° C., 542 g (3.82 mols) of methyl iodide are added and the mixture is stirred for 4 hours at room temperature. The mixture is filtered off with suction and the residue is washed with water and also with petroleum ether and dried at 60° C. in vacuo, after which 748 g (89% of theory) of the above compound of melting point 111°–113° C. are obtained. The purity as determined by gas chromatography is 99%.

A sample recrystallized from a little toluene melts at 114°–115° C.

The following compounds of the formula (Ia) are obtained in an analogous manner

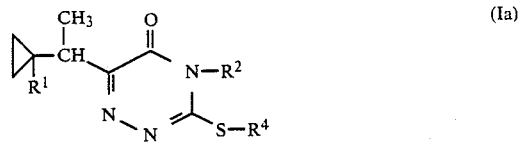

TABLE 1

| Example No. | $R^1$ | $R^2$ | $R^4$ | M.p. (°C.) |
|---|---|---|---|---|
| 2 | H | $NH_2$ | $C_2H_5$ | 109–110 |
| 3 | H | $CH_3$ | $CH_3$ | 64–66 |
| 4 | H | $CH_3$ | $C_2H_5$ | 41–43 |
| 5 | H | $NH-CH_3$ | $CH_3$ | 66–68 |
| 6 | $CH_3$ | $NH_2$ | $CH_3$ | 132 |
| 7 | $CH_3$ | $NH_2$ | $C_2H_5$ | 74–76 |

Example 8

4-Amino-6-(1-cyclopropylethyl)-3-methylamino-1,2,4-triazin-5(4H)-one (according to process B):

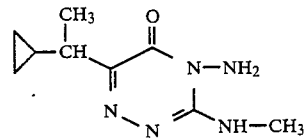

24.0 g (0.1 mol) of 4-amino-6-(1-cyclopropylethyl)-3-ethylthio-1,2,4-triazin-5(4H)-one are dissolved in 60 ml of isopropanol with the addition of 7.2 g of acetic acid and 0.5 g of p-toluenesulphonic acid and, after the introduction of 5.0 g (0.16 mol) of methylamine, the solution is heated overnight in an oil bath at 100° C. After evaporation, the resinous residue is stirred with 100 ml of water and 20 ml of concentrated hydrochloric acid, undissolved constituents are removed by shaking with 50 ml of methylene chloride, and the reaction product is precipitated with 30 ml of a 25% strength aqueous ammonia solution: 13.0 g (62% of theory) of the above compound of melting point 125°–127° C. (from toluene) are obtained.

The following compounds of the formula (Ib) are obtained in an analogous manner:

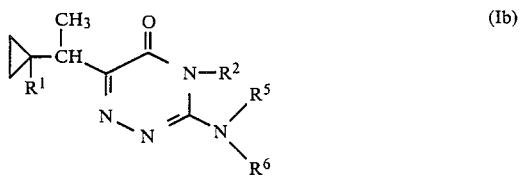

TABLE 2

| Example No. | $R^1$ | $R^2$ | $R^5$ | $R_6$ | M.p. (°C.) [B.pt. (°C./mbar)] |
|---|---|---|---|---|---|
| 9 | H | $NH_2$ | H | $C_2H_5$ | 89–90 |
| 10 | H | $NH_2$ | $CH_3$ | $CH_3$ | 88–90 |
| 11 | H | $CH_3$ | $CH_3$ | $CH_3$ | [112/0.015] |
| 12 | H | $NH—CH_3$ | $CH_3$ | $CH_3$ | [100/0.01] |
| 13 | $CH_3$ | $NH_2$ | H | $CH_3$ | 168 |
| 14 | $CH_3$ | $NH_2$ | H | $C_2H_5$ | 76–79 |
| 15 | $CH_3$ | $NH_2$ | H | $CH_2CH=CH_2$ | 86–88 |
| 16 | $CH_3$ | $NH_2$ | $CH_3$ | $CH_3$ | 70 |

Example 17

6-(1-Cyclopropylethyl)-3-dimethylamino-4-methyl-1,2,4-triazin-5(4H)-one (according to process C):

15.25 g (0.1 mol) of 1-amino-2,2,3-trimethylguanidine hydrochloride and 30 ml of concentrated hydrochloric acid are added to an alkaline saponification solution of cyclopropylmethyl methylene-N-methylrhodanine which contains 0.1 mol of 1-cyclopropylethyl thionoglyoxylic acid, and the mixture is stirred for 1 hour at room temperature and then boiled for 3 hours under reflux. After having cooled to room temperature it is shaken with 50 ml of methylene chloride and the methylene chloride phase is discarded. The aqueous phase is treated with 50 ml of a 25% strength aqueous ammonia solution, the oily reaction product is taken up in methylene chloride and the evaporation residue is distilled in vacuo.

16.0 g of the abovementioned compound are obtained in the form of a pale yellow oil of boiling point 112° C. at 0.015 mbar (72% of theory), identical with a product prepared according to process B (cf. Example 11).

EXAMPLE 18

6-(1-Cyclopropylethyl)-4-methylamino-3-methylthio-1,2,4-triazin-5(4H)-one (according to process D):

100 ml of toluene and 56.5 g (0.25 mol) of 4-amino-6-(1-cyclopropylethyl)-3-methylthio-1,2,4-triazin-5(4H)-one, and then 89.5 g (0.63 mol) of methyl iodide and 8.5 g (0.025 mol) of tetrabutylammonium bromide are added to 100 ml of 50% strength aqueous sodium hydroxide solution with vigorous stirring. The emulsion is stirred vigorously until the exothermic reaction abates (temperature rise to 50° C.). The mixture is filtered with suction through a glass frit at 20° C., the phases are separated and the organic phase is evaporated. The residue is recrystallized from methyl tert.-butyl ether. 32.9 g of the above compound of melting point 66°–68° C., identical with a product prepared according to process A (cf. Example 5), are obtained.

PREPARATION OF THE STARTING MATERIALS 4-(Cyclopropyl-methyl-methylene)-N-methylrhodanine

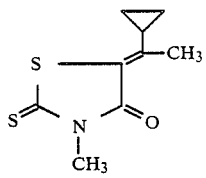

867 g (5.9 mols) of N-methylrhodanine and 555 g (6.54 mols) of cyclopropyl methyl ketone are boiled under reflux in a water separator while 48 g (0.6 mol) of ammonium acetate and 72 g (1.2 mols) of acetic acid in 1 l of benzene are added until the elimination of water ceases (14 hours). The mixture is stirred at 60° C. with 1 l of water, allowed to cool to room temperature and filtered off with suction, and the moist crude product is recrystallized from 4.5 l of ethanol. 1118 g (89% of theory) of the above compound are obtained as an E/Z mixture in a ratio of 60:40, melting range: 85°–97° C.

The following compound is prepared analogously:

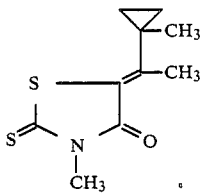

M.p.: 40°–47° C. as the E/Z mixture; the pure E isomer melts at 54° C. (from methanol).

4-Amino-6-(1-cyclopropylethyl)-5-oxo-3-thioxo-tetrahydro-1,2,4-(2H,4H)-triazine

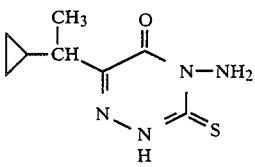

882 g (4.14 mols) of 4-(cyclopropyl-methyl-methylene)-N-methylrhodanine (as an E/Z mixture) are introduced into a solution of 712 g (17.8 mols) of sodium hydroxide in 4.4 l of water. After the addition of 7 ml of alkylaryl polyglycol ether, the mixture is stirred at 70° C. until complete dissolution occurs (about 16 hours). 438 g (4.14 mols) of thiocarbohydrazide and 115 ml of 1-decanol are then added, the mixture is stirred for one hour at 70° C., and 1525 ml of acetic acid are rapidly added dropwise, causing the reaction product to precipitate. The mixture is stirred at 80° C. for a further 2 hours, allowed to cool to room temperature and the precipitate is filtered off with suction, washed several times with water and also with petroleum ether and dried at 70° C. 725 g (82.6% of theory) of the above compound of melting point 142°–143° C. are obtained.

The following compounds are prepared in a similar manner:

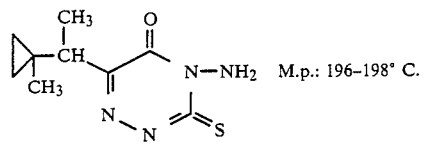 M.p.: 196–198° C.

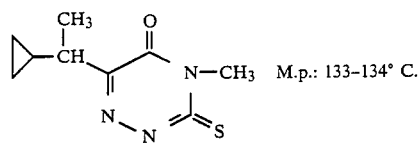 M.p.: 133–134° C.

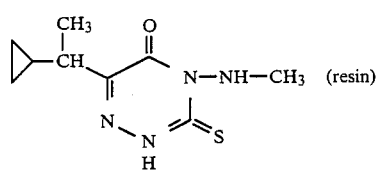 (resin)

1-Methyl-thiocarbohydrazide 142 g (1.17 mols) of methyl dithiocarbazinate are introduced into 300 ml of acetone. After temporary dissolution and a temperature increase to 45° C., 168 g (89% of theory) of methyl isopropylidene-dithiocarbazinate of melting point 115° C. crystallize out.

162 g (1 mol) of this compound are mixed with 190 g (1.2 mols) of 92% strength 1-tert.-butoxycarbonyl-1-methylhydrazine and the mixture is stirred in an oil bath at 110° C. for 8 hours, resulting in the gradual elimination of methyl mercaptan. The 1-tert.-butoxycarbonyl-1-methyl-5-isopropylidene-thiocarbohydrazide which precipitates on cooling is filtered off with suction and washed with toluene. 139 g (53.5% of theory) with a melting range of 165°–172° C. (dec.) are obtained.

130 g (0.5 mol) of this compound are dissolved in 460 ml of semiconcentrated hydrochloric acid, and the solution is stirred for 3 hours at room temperature and evaporated. The residue is dissolved in 460 ml of water and the solution is neutralized with 25% strength ammonia solution and evaporated. The dry residue is boiled several times with methanol. After evaporation of the filtered methanol extract 52.8 g (88% of theory) of 1-methyl-thiocarbohydrazide are obtained as a thick oil.

EXAMPLE A

Post-emergence test
Solvent: 5 parts by weight of acetone
Emulsifier: 1 part by weight of alkylaryl polyglycol ether To produce a suitable preparation of active compound, 1 part by weight of active compound is mixed with the stated amount of solvent, the stated amount of emulsifier is added and the concentrate is diluted with water to the desired concentration.

Test plants which have a height of 5–15 cm are sprayed with the preparation of the active compound in such a way as to apply the particular amounts of active compound desired per unit area. The concentration of the spray liquor is so chosen that the particular amounts of active compound desired are applied in 2,000 l of water/ha. After three weeks, the degree of damage to the plants is rated in % damage in comparison to the development of the untreated control. The figures denote:

0% = no action (like untreated control)
100% = total destruction

In this test the compounds according to the invention display excellent herbicidal activity. Compared with the closest prior art (Metribuzin), the compounds according to preparative Examples 1, 5 (or 18), 8, 10, 12 and 16, for example in this test display far more powerful action against problem weeds, such as, for example, Cassia, Amaranthus, Polygonum, Ipomoea and Solanum, and are at the same time very well tolerated by cultivated plants such as, for example, corn and barley.

EXAMPLE B

Pre-emergence test
Solvent: 5 parts by weight of acetone
Emulsifier: 1 part by weight of alkylaryl polyglycol ether To produce a suitable preparation of active compound, 1 part by weight of active compound is mixed with the stated amount of solvent, the stated amount of emulsifier is added and the concentrate is diluted with water to the desired concentration.

Seeds of the test plants are sown in normal soil and, after 24 hours, watered with the preparation of the active compound. It is expedient to keep constant the amount of water per unit area. The concentration of the active compound in the preparation is of no importance, only the amount of active compound applied per unit area being decisive. After three weeks, the degree of damage to the plants is rated in % damage in comparison to the development of the untreated control. The figures denote:

0% = no action (like untreated control)
100% = total destruction.

In this test the compounds of formula (I) according to the invention also display very powerful action.

It will be understood that the specification and examples are illustrative but not limitative of the present invention and that other embodiments within the spirit and scope of the invention will suggest themselves to those skilled in the art.

We claim:
1. A 3,4,6-trisubstituted 1,2,4-triazin-5(4H)-one of the formula

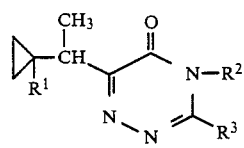

in which
R$^1$ represents hydrogen or methyl,
R$^2$ represents amino, methylamino or methyl and
R$^3$ represents methylthio, ethylthio, methylamino, ethylamino, allylamino, dimethylamino, methylethylamino or diethylamino.
2. A triazinone according to claim 1, in which
R$^1$ represents hydrogen, R² represents amino or methylamino and R³ represents methylthio, methylamino or dimethylamino.

3. A compound according to claim 1, wherein such compound is 4-amino-6-(1-cyclopropylethyl)-3-methylthio-1,2,4-triazin-5(4H)-one of the formula

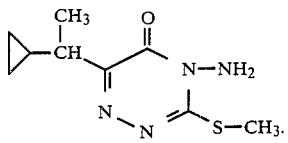

4. A compound according to claim 1, wherein such compound is 4-methylamino-6-(1-cyclopropylethyl)-3-methylthio-1,2,4-triazin-5(4H)-one of the formula

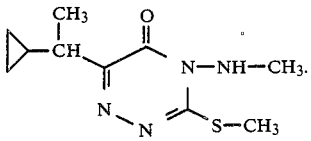

5. A compound according to claim 1, wherein such compound is 4-amino-6-(1-cyclopropylethyl)-3-methylamino-1,2,4-triazin-5(4H)-one of the formula

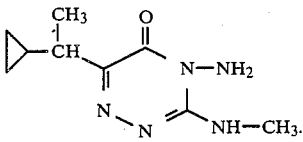

6. A compound according to claim 1, wherein such compound is 4-amino-6-(1-cyclopropylethyl)-3-dimethylamino-1,2,4-triazin-5(4H)-one of the formula

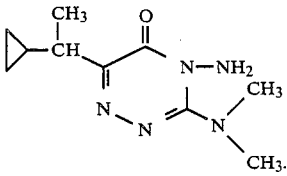

7. A compound according to claim 1, wherein such compound is 4-methylamino-6-(1-cyclopropylethyl)-3-dimethylamino-1,2,4-triazin-5(4H)-one of the formula

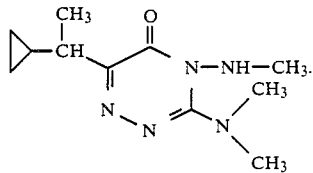

8. A compound according to claim 1, wherein such compound is 4-amino-6-[1-(1-methylcyclopropyl)-ethyl]-3-dimethylamino-1,2,4-triazin-5(4H)-one of the formula

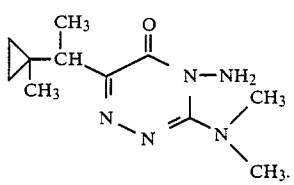

9. A herbicidal composition comprising a herbicidally effective amount of a compound according to claim 1 and a diluent.

10. A method of combating unwanted vegetation which comprises applying to such vegetation or to a locus from which it is desired to exclude such vegetation a herbicidally effective amount of a compound according to claim 1.

11. The method according to claim 11, wherein such compound is
4-amino-6-(1-cyclopropylethyl)-3-methylthio-1,2,4-triazin-5(4H)-one,
4-methylamino-6-(1-cyclopropylethyl)-3-methylthio-1,2,4-triazin-5(4H)-one,
4-amino-6-(1-cyclopropylethyl)-3-methylamino-1,2,4-triazin-5(4H)-one,
4-amino-6-(1-cyclopropylethyl)-3-dimethylamino-1,2,4-triazin-5(4H)-one,
4-methylamino-6-(1-cyclopropylethyl)-3-dimethylamino-1,2,4-triazin-5(4H)-one, or
4-amino-6-[1-(1-methylcyclopropyl)-ethyl]-3-dimethylamino-1,2,4-triazin-5-(4H)-one.

12. A compound of the formula

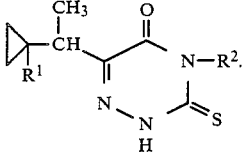

in which
R¹ represents hydrogen or methyl, and
R² represents amino, methylamino or methyl.

* * * * *